United States Patent [19]

Nienhuis

[11] Patent Number: 5,780,447
[45] Date of Patent: Jul. 14, 1998

[54] RECOMBINANT ADENO-ASSOCIATED VIRAL VECTORS

[75] Inventor: Arthur W. Nienhuis, Memphis, Tenn.

[73] Assignee: St. Jude Children's Research Hospital, Memphis, Tenn.

[21] Appl. No.: 663,947

[22] Filed: Jun. 14, 1996

[51] Int. Cl.$^6$ .................... A01N 63/00; A61K 48/00; C12N 5/00; C12N 15/00
[52] U.S. Cl. .................... 514/44; 424/93.2; 424/93.21; 435/172.3; 435/320.1; 435/325; 435/375; 935/22; 935/34; 935/62
[58] Field of Search .................... 514/44; 424/93.1, 424/93.2, 93.21; 435/240.2, 320.1, 172.3, 325, 375; 536/23.5, 24.1, 24.5; 935/22, 33, 34, 62

[56] References Cited

U.S. PATENT DOCUMENTS 5,252,479  10/1993  Srivastava.

OTHER PUBLICATIONS

E. Marshall (1995) Science 269: 1050–1055.
Ville et al. (1995) Targeted Gene Therapy 9: 190–199.
Li and Stamatoyannopoulos, "Position Independence and Proper Developmental Control of γ-Globin Gene Expression Require both a 5' Locus Control Region and a Downstream Sequence Element", *Mol. Cell. Biol.* 14:6087–6096 (1994).
Walsh et al., "Regulated high level expression of a human γ-globin gene introduced into erythroid cells by an adeno–associated virus vector", *Proc. Natl. Acad. Sci. USA* 89: 7257–7261 (1992).
Miller et al., "Recombinant adeno–associated virus (AAV)–mediated expression of a human γ-globin gene in human progenitor–derived erythroid cells", *Proc. Natl. Acad. Sci. USA* 91: 10183–10187 (1994).
Cunningham et al., "The Regulatory Element 3' to the $^A$γ-Globin Gene Binds to the Nuclear Matrix and Interacts With Special A–T–Rich Binding Protein 1 (SATB1), an SAR/MAR-Associating Region DNA Binding Protein", *Blood* 84: 1298–1308 (1994).
Bodine and Ley, "An enhancer element lies 3' to the human Aγ globin gene", *EMBO J.* 6: 2997–3004 (1987).
Walsh et al., "Gene Therapy for Human Hemoglobinopathies", *P.S.E.B.M.* 204: 289–300 (1993).
Goodman et al., "Recombinant Adeno–Associated Virus–Mediated Gene Transfer Into Hematopoietic Progenitor Cells", *Blood* 84: 1492–1500.

*Primary Examiner*—Bruce R. Campbell
*Attorney, Agent, or Firm*—Needle & Rosenberg, PC

[57] ABSTRACT

The present invention provides a vector comprising an enhancer element and a nuclear matrix association region inserted between an inverted terminal repeat of adeno-associated virus. The vector can further comprise a heterologous nucleic acid inserted into the vector. The present invention further provides a method for integration of a nucleic acid into the genome of a cell, comprising administering to the cell a vector comprising an enhancer element, a heterologous nucleic acid and a nuclear matrix association region, each inserted between an inverted terminal repeat of adeno-associated virus, thereby integrating the nucleic acid into the genome of the cell.

39 Claims, 9 Drawing Sheets

RECOMBINANT ADENO-ASSOCIATED VIRAL VECTORS

This invention was made with government support under Program Project Grant P01 HL 53749 awarded by NHLBI. The government has certain rights in the invention.

BACKGROUND OF THE INVENTION

1. Field of the Invention

The present invention is related to the field of nucleic acid delivery vectors and methods of delivering nucleic acids. In particular it relates to vectors for integration of nucleic acids at high copy number and in tandem array, and therefore it relates to methods of stable expression of transferred nucleic acids in cells into which the vector has been transferred. The present method thus also relates to the field of ex vivo transfer of nucleic acids into cells for transplantation into a subject.

2. Background Art

Adeno-associated virus (AAV) is a single stranded DNA virus with a 4675 nucleotide genome. AAV depends on co-infection with a helper DNA virus, e.g., adenovirus or a herpes virus, which provides functions needed in trans for AAV genome replication and encapsidation (13–16; 87). The wild-type AAV genome preferentially integrates into a specific region of chromosome 19 by a mechanism that depends on its non-structural (Rep) proteins (17,18). Only the 145 nucleotide inverted terminal repeats (ITRs) are required in cis to generate a rAAV vector; the Rep and capsid proteins can be provided in trans in packaging cells that are also expressing adenoviral proteins (13–16). The inverted terminal repeat of AAV consists of nucleotides 1 to 145 at the left end of the AAV genome and the corresponding nucleotides 4681 to 4536 at the right end of the genome. These elements are utilized in replicating, packaging and integrating AAV into a host genome. Additionally, the ITRs have been shown to have intrinsic promoter capabilities. Recent advances have provided packaging systems that yield purified rAAV preparations of relatively high titer (19–21).

While rAAV vectors have been shown to transfer, integrate and express globin genes in erythroleukemia cells when linked to a drug selection marker that facilitates recovery of clonal cell lines (22–24), the frequency of rAAV transduction and genomic integration was not established with this experimental design because selection allows recovery of resistant clones even at low efficiencies of transduction and integration. Drug selection also demands that the rAAV genome be integrated into a transcriptionally active region of chromatin that is also likely to be permissive for globin gene expression. While AAV has been proposed as a vector for gene therapy, expression levels adequate to treat a disease have remained problematic. Expression of a globin gene has been observed in primary, progenitor derived erythroid colonies without drug selection (25). However, available data have shown that an episomal rAAV genome may only express its encoded genes for several days (26–28), raising the likelihood that the globin MRNA found in erythroid colonies 14 days after transduction of purified hematopoietic progenitors was derived from a non-integrated genome.

An rAAV encoding the murine ecotropic receptor has been used to evaluate the relationship between initial gene expression and subsequent genome integration (28). Ecotropic retroviruses infect mouse but not human cells because of interspecies polymorphism in the cationic amino transporter that acts as a receptor for this class of viruses (34). This evaluation showed that human HeLa cells could be transduced at a ratio of rAAV vector particles of approximately 300 to 30,000, leading to expression of the receptor protein, permitting subsequent infection by an ecotropic retrovirus (28). Under these conditions, however, integration of the rAAV genome occurred infrequently and only at higher MOI. Supporting this interpretation is the finding associated with this invention that the rAAV genome, although present initially following engraftment of transduced bone marrow cells, may disappear during long-term reconstitution in a non-human primate, bone marrow transplantation model.

Human hemoglobin (Hb) disorders such as thalassemia and sickle-cell disease are a cause of significant morbidity and mortality worldwide. Therapeutic strategies directed toward genetic modification involve replacement of the defective gene via allogenic bone marrow transplantation or the addition of a functional gene to the defective bone marrow cells. Hemoglobin F ($\alpha_2\gamma_2$) is the major Hb during the last two thirds of gestation. The shift from HbF to HbA ($\alpha_2\beta_2$) during the prenatal period reflects turn-off of the $\gamma$ genes and turn-on of the $\beta$ genes. This switch initiates disease in individuals homozygous for defective $\beta$ genes, e.g., those with mutations that cause sickle-cell anemia or severe $\beta$-thalassemia. Provision of a functional $\gamma$ globin gene to such individuals such that the individual can increase their HbF content is of therapeutic benefit.

Therefore, the ability to transfer a globin gene into repopulating hematopoietic stem cells and to achieve its expression in differentiating erythroid cells could serve as a gene therapy for severe $\beta$-thalassemia and sickle cell anemia. Attempts to develop retroviral vectors for this purpose have been hampered by the relative inefficiency of gene transfer by such vectors into stem cells (1–5). Furthermore, the regulatory elements derived from the locus control region (LCR) that are required to achieve high level expression of a linked globin gene cause proviral genome instability during virus production and transfer of the retroviral genome (3,6,7). Only recently have stable retroviral vectors been derived that are capable of transferring a globin gene with regulatory elements into primary hematopoietic cells or cell lines (8–11). Unfortunately, the long terminal repeats of the integrated retroviral genome may cause suppression of globin gene expression in erythroid cells (12).

Nuclear matrix association regions have been identified in various genomes, including the eight nuclear scaffold/matrix associating regions (SARs/MARs) found within the 90 kb of DNA that flanks and includes the human globin genes (42) SARs/MARs have been hypothesized to influence chromatin structure (reviewed in 43), serve as boundaries between transcriptional domains (44, 45), and/or establish loops of DNA that serve to juxtapose distant sequences (43, 46).

Thus, there remains a need for vectors which can provide adequate functional gene copy numbers for the successful treatment of various diseases. The present invention satisfies this need by providing the surprising discovery that an AAV vector comprising a nuclear matrix association region provides a vector that can stably integrate a cellular genome with a transferred gene in unrearranged form, with multiple copy number and in tandem array. Such a vector is therefore highly useful for methods in which long-term, stable expression is desired. Such a method also allows transfer of nucleic acids into non-dividing cells and therefore is particularly suitable for transfer into hematopoietic stem cells.

SUMMARY OF THE INVENTION

The present invention provides a vector comprising an enhancer element and a nuclear matrix association region inserted between an inverted terminal repeat of adeno-associated virus. The vector can further comprise a heterologous nucleic acid inserted into the vector. The invention further provides a particle containing vector of the present invention, a composition containing a particle of the invention and a cell containing a particle of the invention.

The present invention further provides a vector comprising a globin gene cluster hypersensitive element, the 3' regulatory element of γ globin, and a nucleic acid encoding a protein, each inserted between an inverted terminal repeat of adeno-associated virus such that the nucleic acid encoding the protein can be expressed.

The instant invention additionally provides a vector for integration and expression of a protein comprising a globin gene cluster hypersensitive element, a 3' regulatory element of γ globin, and a nucleic acid encoding a protein, each inserted between an inverted terminal repeat of adeno-associated virus, wherein the nucleic acid encoding the protein is inserted 3' of the hypersensitive element and 5' of the 3' regulatory element.

The present invention further provides a method for integration of a nucleic acid into the genome of a cell, comprising administering to the cell a vector comprising an enhancer element, a heterologous nucleic acid and a nuclear matrix association region, each inserted between an inverted terminal repeat of adeno-associated virus, thereby integrating the nucleic acid into the genome of the cell.

The present invention further provides a method for integration of a globin gene into the genome in a cell, comprising administering to the cell a vector comprising a globin gene cluster hypersensitive element, a 3' regulatory element of γ globin, and a nucleic acid encoding globin, each inserted between an inverted terminal repeat of adeno-associated virus, wherein the nucleic acid encoding globin is inserted 3' of the hypersensitive element and 5' of the 3' regulatory element, thereby integrating the globin gene into the genome in the cell. The cell can be a hematopoietic stem cell.

The instant invention additionally provides a method of expressing a protein in a subject comprising administering to the subject a cell to which has been administered ex vivo a vector comprising a globin gene cluster hypersensitive element, the 3' regulatory element of γ globin, and a nucleic acid encoding the protein, each inserted between an inverted terminal repeat of adeno-associated virus such that the nucleic acid encoding the protein can be expressed, thereby expressing the protein in the cell in the subject.

The present invention additionally provides a method of providing a functional protein to a subject in need of the functional protein comprising transducing the subjects' cells with a vector comprising an enhancer element, a heterologous nucleic acid encoding a functional protein deficient in the subject and a nuclear matrix association region, each inserted between an inverted terminal repeat of adeno-associated virus, thereby providing the functional protein to the subject.

The present invention further provides a method of providing an antisense nucleic acid to a subject in need of the antisense nucleic acid comprising transducing the subjects' cells with a vector comprising an enhancer element, a heterologous nucleic acid and a nuclear matrix association region inserted between an inverted terminal repeat of adeno-associated virus, wherein the nucleic acid encodes an antisense nucleic acid that diminishes expression of a protein in the subject, thereby providing the antisense nucleic acid to a subject in need of the antisense nucleic acid.

The present invention additionally provides a method of treating, in a subject, a hemoglobin disorder characterized by a reduction or absence of a functional globin protein, comprising administering to the subject a hematopoietic cell to which has been administered ex vivo a vector comprising a globin gene cluster hypersensitive element, a 3' regulatory element of γ globin, and a nucleic acid encoding functional globin, each inserted between an inverted terminal repeat of adeno-associated virus, wherein the nucleic acid encoding the globin is inserted 3' of the hypersensitive element and 5' of the 3' regulatory element, thereby expressing globin in the cell in the subject and providing functional globin protein to treat the subject.

DETAILED DESCRIPTION OF THE INVENTION

Figure 1A:
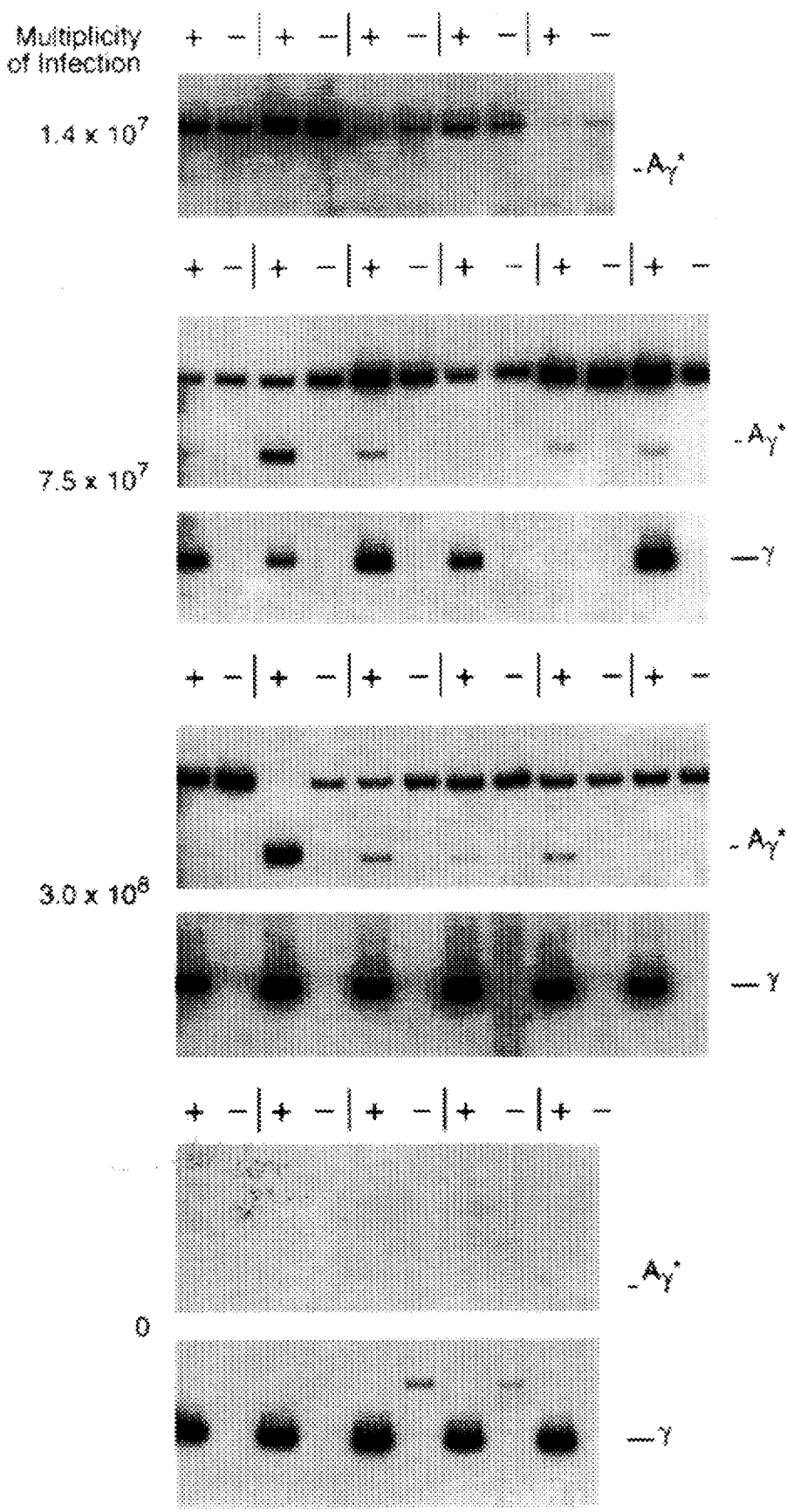
FIG. 1 shows rHS432$^A$γ* mediated gene transfer and expression in primary, progenitor derived, human erythroid colonies. CD34 selected bone marrow cells were exposed to rAAV at various multiplicities of infection, cultured and individual colonies analyzed for mRNA at 14–16 days. The diagram below shows the design of the RT-PCR analysis; the upper band (369 bp) when present is derived from genomic or vector DNA regardless of the use of reverse transcriptase (+ or −) whereas the lower (254 bp) reverse transcriptase dependent band (+) is derived from processed globin MRNA. The 5' primer designed to detect the $^A$γ* RNA spans a 6 base pair deletion in the 5' untranslated region (diagram below) whereas the 5' primer designed to detect the wild-type γ MRNA includes the deleted sequences (not shown).

As used in the specification and in the claims, "a" can include multiple copies, depending upon the context in which it is used.

The present invention provides the discovery that an adeno-associated virus (AAV) vector containing a γ globin gene and a nuclear matrix association region can transduce human hematopoietic cells with high efficiency leading to genomic integration of high copy numbers and persistent gene expression. Thus, the present invention therefore provides a vector into which can be inserted any nucleic acid of interest for integration and expression in a cell into which the vector is transferred. Because this vector provides for integration into the host cell genome, and provides this integration in primarily unrearranged form, at high copy number and in tandem array, this vector is particularly suitable for long-term, stable expression of gene products.

Specifically, the present invention provides a vector comprising an enhancer element and a nuclear matrix association region inserted between an inverted terminal repeat of AAV. In such a vector, a desired nucleic acid can be inserted between the inverted terminal repeat of AAV such that the nucleic acid is functionally linked with the enhancer element for enhancing transcription of the encoded gene product and functionally linked with the nuclear matrix association region such that the nucleic acid integrates into the genome of a target cell in unrearranged form, in multiple copy number and, preferably, in tandem array. The nucleic acid can preferably be inserted 5' to the nuclear matrix association region. The inserted nucleic acid can include any additional desired expression control sequences, as known in the art and described herein.

The nuclear matrix association region can be any nucleic acid fragment that is capable of associating with the nuclear matrix. Examples of such a region includes the γ globin 3' regulatory element (3RE) (29, 47), other nuclear scaffold/matrix-associated regions of the human globin gene locus (48); matrix attachment region of immunoglobulin (49); matrix attachment regions of chromosomal continuum containing maize Adh1 (50); intragenic matrix attachment region in human X-linked Hprt gene (51); matrix attachment region (52); Msp 18 (53); (54); highly repetitive DNA components of rat-ascites hepatoma cells (55); NuMA (56); region recognized by nucleolin (57); MAR of chicken γ-globin gene (58); immunoglobulin mu gene nuclear MARs (59); intronic nuclear MARs in human topoisomerase I gene (60); intronic MAR of immunoglobulin kappa gene (61); recognition site for SATB1 (62); matrix attachment region 5' of rat glutamate-dehydrogenase-encoding gene (63); nuclear MARs along human β globin gene complex (64); MAR in yeast (65); nuclear MAR associated with osteocalcin gene (66); additional nuclear MARs reviewed (67). Additionally, other primates may have nuclear matrix association regions in the globin locus. Additional nuclear matrix association regions can readily be determined by performing a nuclear scaffold/matrix association assay, as known in the art (29). Additionally, these nuclear matrix association regions must possess the function of causing integration into a host genome in multiple copy number of a vector in which they are inserted. Known nuclear matrix association regions can be modified to create additional nuclear matrix association elements for use in the present vectors, so long as they retain the function of binding to the nuclear matrix. For example, nucleotide deletions, substitutions and or additions can be made, according to standard methods for nucleic acid manipulation. If desired, for example, the 3'RE of globin can have a systematic set of deletions made and assayed for retention of nuclear matrix binding function to determine the minimum element necessary. Such general methods are well established (33).

The present vector can further comprise an enhancer element. An enhancer element is an element that increases transcription from a linked promoter. The enhancer element as used in the claims is an element of the vector which is provided in addition to the nuclear matrix association region. However, the nuclear matrix association region γ globin 3' RE can itself act as an enhancer element. An enhancer can include, for example, one or more hypersensitive elements of the globin gene cluster, such as the human globin HS4, HS3, HS2, and/or HS 1 element or a hypersensitive element derived from another primate. Additional enhancers can include viral elements, elements from the U3 region of retroviral long terminal repeats (such as Friend murine leukemia virus), the immunoglobulin enhancer element (68), the insulin receptor enhancer element (69), the c-fos enhancer element, human growth hormone enhancer element (70); apolipoprotein E and C-I gene enhancer element (71); the albumin/alpha 1-fetoprotein intergenic enhancer (72); Drosophila zeste mutations having enhancer effect (73); and others (74).

Any nucleic acid of interest can be inserted into a vector of this invention. Thus, the vector can additionally advantageously include a restriction enzyme recognition site for ease of inserting an exogenous nucleic acid into the vector in a region such that the nucleic acid is functional for expression of the gene product. A vector having an inserted nucleic acid of interest can be utilized for achieving integration and expression of the nucleic acid in a cell into which the vector is transferred. In particular, such a vector can achieve integration in multiple, high copy number in tandem array. The integrated nucleic acids being unrearranged, the encoded gene product can then be expressed, particularly and beneficially at high levels. Such methods are well known in the art (33).

The nucleic acid encoding a desired protein or antisense RNA can be any nucleic acid that functionally encodes the protein or antisense RNA. For example, to functionally encode, i.e., allow the nucleic acid to be expressed, the nucleic acid can include, for example, expression control sequences, such as a promoter, and necessary information processing sites, such as ribosome binding sites, RNA splice sites, polyadenylation sites, and transcriptional terminator sequences. Expression control sequences can include, for example, promoters derived from metallothionine genes, actin genes, immunoglobulin genes, CMV, SV40, adenovirus, bovine papilloma virus, etc.

A nucleic acid encoding a selected protein can readily be determined based upon the genetic code for the amino acid sequence of the selected protein, and, clearly, many nucleic acids will encode any selected protein. Additionally, modifications can be made to any nucleic acid, such as modifications to the sequences controlling expression of the protein to make production of the protein inducible or repressible upon addition to the cells of the appropriate inducer or repressor. Such means are standard in the art (33). The nucleic acids can be generated by means standard in the art, such as by recombinant nucleic acid techniques, as exemplified in the examples herein, and by synthetic nucleic acid synthesis or in vitro enzymatic synthesis.

Nucleic acids encoding any selected protein or antisense construct can be utilized in the present vectors. For example, nucleic acids encoding a globin from human or another primate can be used, such as a globin, β globin, γ globin, δ globin, ε globin or ψβ globin (29); metabolic enzymes, such as adenosine deaminase (U.S. Pat. No. 5,399,346); cytokines; anti-viral elements, such as ribozymes and transdominant mutants of viral proteins; growth factors, such as erythropoietin; proteins which may ameliorate neurological disorders such as: sequences encoding nerve growth factor (NGF), ciliary neurotrophic factor (CNTF), brain-derived neurotrophic factor (3DNF), neurotrophins 3 and 4/5 (NT-3 and 4/5), glial cell derived neurotrophic factor (GDNF), transforming growth factors (TGF), and acidic and basic fibroblast growth factor; sequences encoding tyrosine hydroxylase (TH) and aromatic amino acid decarboxylase (AADC); sequences encoding superoxide dismutase (SOD 1 or 2), catalase and glutathione peroxidase; sequences encoding interferons, lymphokines, cytokines and antagonists thereof such as tumor necrosis factor (TNF), CD4 specific antibodies, and TNF or CD4 receptors; sequences encoding GABA receptor isoforms, the GABA synthesizing enzyme glutamic acid decarboxylase (GAD), calcium dependent potassium channels or ATP sensitive potassium channels; and sequences encoding thymidine kinase can be utilized.

In a specific embodiment, the present invention includes a vector for integration and expression of a globin comprising a globin hypersensitive element, a 3' regulatory element of γ globin, and a nucleic acid encoding a globin, each inserted between an inverted terminal repeat of adeno-associated virus, wherein the nucleic acid encoding the globin is inserted 3' of the hypersensitive element and 5' of the 3' regulatory element.

Recombinant vectors can also include nucleic acids that encode antisense nucleotides that affect expression of certain genes such as cell death suppressor genes (e.g., bcl-2) or that affect expression of excitatory amino acid receptors (e.g., glutamate and NMDA receptors). Further antisense RNAs that can be generated by the present vectors include c-myc, c-myb, CDC2 and PCNA antisense RNAs, known to be cytotoxic or inhibitory to cell proliferation when transfected into cells.

The terms "polypeptide" and "protein" are used interchangeably herein and refer to a polymer of amino acids and includes full-length proteins and fragments thereof. As will be appreciated by those skilled in the art, the invention also includes nucleic acids that encode those polypeptides having slight variations in amino acid sequences or other properties from a known amino acid sequence. Amino acid substitutions can be selected by known parameters to be neutral (75) and can be introduced into the nucleic acid sequence encoding it by standard methods such as induced point, deletion, insertion and substitution mutants. Minor changes in amino acid sequence are generally preferred, such as conservative amino acid replacements, small internal deletions or insertions, and additions or deletions at the ends of the molecules. Substitutions may be designed based on, for example, the model of Dayhoff et al. (86). These modifications can result in changes in the amino acid sequence, provide silent mutations, modify a restriction site, or provide other specific mutations. Additionally, they can result in a beneficial change to the encoded protein. For example, the γ globin gene can be altered such that the protein has beneficial properties in gene therapy.

The present examples exemplify a viral vector utilizing AAV. However, one can readily utilize other suitable viral vectors. Upon selection of a virus and construction of a vector comprising an enhancer element and a nuclear matrix association region inserted into the viral vector, along with a nucleic acid of interest, one can readily determine whether the particular virus selected can also achieve desired levels of integration in multiple copy number and in tandem array by utilizing a nuclear matrix association region adapted for the particular virus. The nucleic acid encoding a protein or antisense RNA of choice can be inserted by standard means into a region of the viral genome suitable for insertion of an exogenous gene, as is known in the art for each individual virus. Thus one can develop viral vectors suitable for a selected cell type. Viruses whose sequences can be thus utilized can include any desired virus, such as adenovirus, herpesvirus, or hepatitis viruses.

The present invention additionally provides a particle containing the vector of this invention. The particle can be selected according to the viral sequences utilized in construction of the vector. Several methods are known for encapsidating AAV genomes to generate recombinant AAV viral particles; these methods can be utilized to package the present AAV vectors. For example, as known in the art, helper virus, such as adenovirus or herpes simplex virus, can be utilized to package an AAV virus (76, 77, 87). Infection of a cell containing a vector of the invention with AAV helper virus results in packaging of the rAAV. Means of packaging any specific virus of interest are standard and known in the art.

The present invention additionally provides a composition comprising a particle of this invention. Such a composition can include, for example, a pharmaceutically acceptable carrier or other medicinal agents, pharmaceutical agents, carriers, adjuvants, diluents, etc. Thus such a composition can be used, for example, in transfection of a cell ex vivo or in administering a viral particle directly to a subject. Other components of a herein described composition can include, for example, protamine sulfate, calcium phosphate and/or polylysine glycerol. By "pharmaceutically acceptable" is meant a material that is not biologically or otherwise undesirable, i.e., the material may be administered to an individual along with the selected vector without causing any undesirable biological effects or interacting in a deleterious manner with any of the other components of the pharmaceutical composition in which it is contained.

The present invention additionally provides a cell containing a vector of this invention. The cell can be any selected cell or cell line into which the vector can be transferred. AAV has a broad host range (15). Methods of transfer are standard in the art and additionally are further elaborated herein. Preferred cells are mammalian cells, for example, cells derived directly from a mammalian subject, such as neurons, hepatocytes, lymphocytes, and muscle cells. Preferable cells also include stem cells, and even more preferably, hematopoietic stem cells. For example, bone marrow cells can be beneficially transfected ex vivo by this method prior to transfer into a subject. Additionally, the cells can be a cell line, such as a human erythroleukemia cell line (e.g., K562) or a HeLa cell line.

The present invention additionally provides a method for integration of a nucleic acid into the genome in a cell, comprising administering to the cell a vector comprising an enhancer element and a nuclear matrix association region inserted between an inverted terminal repeat of adeno-associated virus and further comprising the nucleic acid inserted into the vector, thereby integrating the nucleic acid into the genome of the cell. The nucleic acid is inserted into the vector in a functional manner, i. e., such that the nucleic acid can be expressed from the vector. The vector can be administered at a high multiplicity of infection (m.o.i.). A high m.o.i. can increase the number of clones in which the integration in tandem array can be achieved, presumably by increasing viral particle uptake and/or increasing the conversion of single-stranded AAV DNA to double stranded AAV DNA. The method can also be performed wherein the vector is administered in the absence of drug selection. This method achieves integration in multiple tandem copies, and thus achieves a high level of expression of the inserted nucleic acid. Therefore, therapeutic levels of an encoded gene product can be obtained utilizing the present method.

The multiplicity of infection (m.o.i.) can be varied according to the cell transfected with the vector. A m.o.i. should be used that is sufficient to obtain sufficient levels of expression of the nucleic acid encoded by the vector transferred into the cell. In general, a m.o.i. of from about $3.0 \times 10^2$ to about $3.0 \times 10^{10}$ can be utilized. Preferably a high multiplicity of infection can be used. A high multiplicity of infection is a level of infection understood in the art; however, typically a high m.o.i. will be $10^2$ or higher. The m.o.i., however, can be optimized for the specific cell utilized. For example, a m.o.i. can be $10^3$, more preferably $10^4$, more preferably $10^5$, more preferably $10^6$, more preferably $10^7$, more preferably $10^8$ or $10^9$. For a specific example, for K562 cells, a preferable m.o.i. is from about $10^8$ to about $10^{10}$, with a typical m.o.i. being about $4 \times 10^9$. For a hematopoietic stem cell, a preferred m.o.i. is from about $10^8$ to about $10^{10}$, with a typical m.o.i. being about $10^{10}$. In general, for a cell to be transfected ex vivo the m.o.i. can be optimized by culturing a portion of the cells to be transfected with the particular viral particle in a range of m.o.i.'s (such as from about $3.0 \times 10^2$ to about $3.0 \times 10^9$) and determining at which m.o.i. integration was achieved in multiple copy number.

M.o.i. necessary for any transfection can be dependent upon the purity of the viral stock being administered to the cell. For example, contaminating viruses that are not functional in this method may be present in the stock and can thus increase or reduce the m.o.i. needed for sufficient integration and expression. Thus purification of the stock can lower the m.o.i. used. Additionally, the viral particle could be administered to a cell in a mixture with or simultaneously with another viral particle that would facilitate integration of the vector into the genome. For example, an AAV particle can be administered in a mixture or simultaneously with an AAV encoding an adenoviral protein, such as ORF6 of the E4 region, that would facilitate conversion of the vector nucleic acid from a single stranded nucleic acid to double stranded. Such a strategy can be used to decrease the multiplicity of infection necessary to achieve sufficient integration into the genome.

Other methods for reducing the multiplicity of infection necessary to achieve a desired level of integration can include pretreatment with heat shock, for example, at 42.5° C. for 30 minutes, or pretreatment with hydroxyurea at 10 mM for 24 hours, by standard methods (78). Briefly, for heat shock pretreatment, the medium is exchanged for medium preheated to 42.5° C. and the cells incubated for 30 minutes. Immediately following heat shock, the cells are infected as usual. For hydroxyurea pretreatment, the medium is supplemented with hydroxyurea to a final concentration of 10 mM. The cells are then infected as usual.

The present invention additionally provides a method for integration of a globin gene into the genome in a cell, comprising administering to the cell the vector comprising a globin hypersensitive element, the 3' regulatory element of γ globin, and a nucleic acid encoding a globin, each inserted between an inverted terminal repeat of adeno-associated virus such that the globin gene can be expressed. The globin can be any desired globin, such as γ globin, and is preferably a human globin. This method achieves integration in multiple tandem copies, and thus achieves a high level of expression of the inserted nucleic acid. Therefore, therapeutic levels of globin can be obtained utilizing the present method. For example, the method can be used to express a globin gene in a hematopoietic stem cell and the stem cell transferred into a subject having a deficiency in the globin, such a subject having β-thalassemia or sickle-cell anemia.

Administration of the vector to the cell can be accomplished by any means, several of which are standard in the art. Preferably, the vector is packaged into a viral particle, by the means appropriate for the specific viral sequences utilized in the vector, and the viral particle is added to the cells at the appropriate multiplicity of infection.

Administration to the cells can be performed according to standard transduction methods for the particular cells. For example, for administration to stem cells generally, the bone marrow from a subject for autologous or allogenic transplantation is purified for hematopoietic stem cells. Various methods for purifying the stem cells to various levels are known in the art, see, eg., U.S. Pat. Nos. 4,714,680; 4,965, 204; 5,035,994; 5,004,681; 5,192,553; 5,087,570; 5,061, 620. For administration to autologous bone marrow in particular, a portion of marrow harvested from a subject can be incubated for, e.g., about 6 hours with vector (such as supernatant collected from cells containing the vector and infected with helper virus to package). This aliquot can then typically be frozen until administration into the subject.

The present method of integration also includes that the administration of the vector to the cell is performed in the absence of drug selection. Following adminstration of the vector, the vector integrates into the genome without a need for drug selection.

Specifically, the present method can include administering to a cell a vector that encodes a globin gene, and can specifically encode a γ globin gene. The method can be used to administer specifically a human globin. Preferably, a cell having a globin gene integrated into its genome by the present ex vivo method, for use in transferring the cell into a patient to treat a hemoglobin disorder, will have at least about four copies of the globin gene.

The present method can be used to transduce a cell ex vivo, which cell can then be transferred into a subject to thereby express the inserted nucleic acid for therapeutic benefit. The cell, such as a hematopoietic stem cell or other stem cell, can be transduced by the methods described herein using the present vector encoding the protein of interest, such as a globin. The cell is then transplanted into the subject using methods which are well known in the art (U.S. Pat. No. 5,399,346). Other cells of interest that can be utilized for such gene therapy methods are described herein, and include, for example, neuronal cells, hepatocytes, lymphocytes and muscle cells. Once the cells have been transduced with a vector of the invention encoding a gene of interest, the cells are transplanted into the subject following the appropriate protocol known in the art for that organ, tissue or cell type. For example, transplant of bone marrow is well established (79; U.S. Pat. No. 5,399,346).

Thus, the present invention includes a method of expressing a globin in a subject comprising administering to the subject a cell to which has been administered ex vivo a vector for integration and expression of a globin comprising a globin hypersensitive element, a 3' regulatory element of γ globin, and a nucleic acid encoding a globin, each inserted between an inverted terminal repeat of adeno-associated virus, wherein the nucleic acid encoding the globin is inserted 3' of the hypersensitive element and 5' of the 3' regulatory element, thereby expressing the globin in the cell in the subject.

The present method additionally provides a method of providing a functional protein to a subject in need of the functional protein, comprising transducing the subjects' cells with a vector comprising an enhancer element, a nuclear matrix association region and a nucleic acid encoding a functional protein deficient in the subject inserted between an inverted terminal repeat of adeno-associated virus, thereby providing the functional protein to the subject. Examples of such protein include a globin and cytosine deaminase. The subjects' cells can be transduced either in vivo or ex vivo.

The AAV vectors can also be administered in either in vivo or ex vivo gene therapy procedures in various other formulations in which the vector plasmid is administered as free DNA either by direct injection or after incorporation into other delivery systems such as liposomes or systems designed to target by receptor-mediated or other endocytosis procedures. The AAV vector can also be incorporated into an adenovirus, retrovirus or other virus which can be used as the delivery vehicle.

If ex vivo methods are employed, the transduced cells are then infused or homotopically transplanted back into the subject per standard methods for the cell type. Standard methods are known for transplantation or infusion of various cells into a subject. For example, for neuronal cell transplantation, see (80); for bone marrow infusion, see U.S. Pat. No. 5,399,346; (79, 5); for myoblast transplantation, see (82, 83, 84, 88). The present method can be optimized for hematopoietic stem cells, for example, by using immunodeficient mice in which relatively small numbers of human repopulating cells can be assayed (40,41).

For in vivo administration of the vector, the AAV particle can be directly injected intravenously. The AAV has a broad host range, so the vector can be utilized to transduce any of several cell types, but preferably cells in those organs that are well perfused with blood vessels. To more specifically administer the vector, the AAV particle can be directly injected into the target organ, such as muscle, the liver or kidney. To preferentially administer to the lungs, the AAV particle can, for example, be administered as an inhaled aerosol or injected intratracheally. Furthermore, the vector can be administered intraarterially, directly into a body cavity, such as intraperitoneally, or directly into the CNS.

The present invention additionally provides an antisense nucleic acid to a subject in need of the antisense nucleic acid comprising transducing the subjects' cells with a vector comprising an enhancer element, a nuclear matrix association region and a nucleic acid encoding an antisense nucleic acid that diminishes expression of a protein in the subject inserted between an inverted terminal repeat of adeno-associated virus, thereby providing the antisense nucleic acid to a subject in need of the antisense nucleic acid. As described above, the subjects' cells can be transduced either in vivo or ex vivo.

The present invention further provides a method of treating, in a subject, a hemoglobin disorder characterized by a reduction or absence of a functional globin protein, comprising administering to the subject a hematopoietic cell to which a vector, comprising a globin hypersensitive element, the 3' regulatory element of γ globin, and a nucleic acid encoding a globin, each inserted between an inverted terminal repeat of adeno-associated virus such that the globin gene can be expressed, has been administered ex vivo, thereby expressing globin in the cell in the subject and providing functional globin protein to treat the subject. Thus the hematopoietic cell will have multiple integrated copies of the globin gene in tandem array, thus allowing expression of the globin gene in beneficial quantity. The appropriate globin gene can be selected and inserted into the vector for transfer into a cell ex vivo, which cell can then be administered to the subject to provide the encoded protein, as described herein. For example, γ globin can be inserted into the vector.

The subject for any ex vivo or in vivo treatment can be any animal, preferably a mammal, such as a human, a veterinary animal, such as a cat, dog, horse, pig, goat, sheep, or cow, or a laboratory animal, such as a mouse, rat, rabbit, or guinea pig.

The present vectors may be adapted for various purposes. Adaptation of the present rAAV vectors for therapeutic purposes can be made based upon the mechanisms that control transduction, gene expression and genomic integration. For example, viral uptake may depend on receptor number and it could account in part for the $10^4$ higher MOI found to be required for transduction of hematopoietic cells compared to HeLa cells (28). Furthermore, once in the cell, the single stranded rAAV genome must be converted into a double stranded, transcriptional template (27). There appears to be a correlation between the level of rAAV encoded gene expression during the first 1–3 days after exposure of target cells to rAAV and the amount of double stranded episomal AAV genome. The adenoviral gene products encoded by E1 and E4 (open reading frame 6) enhance the conversion of single stranded rAAV DNA into its double stranded form (27). Thus one may increase expression of cellular genes that facilitate DNA synthesis utilizing these adenoviral proteins.

Furthermore, exposure of cells to DNA synthesis inhibitors and DNA damaging agents (35) may also enhance transcription of a rAAV genome, presumably by triggering DNA repair mechanisms that facilitate its conversion to a double stranded form. The higher transduction frequencies observed in cycling versus quiescent cells (36) and immortalized versus primary cells (37) might also be accounted for by the relative efficiency of the conversion of the rAAV genome into its double stranded form. Formation of double stranded DNA could also occur by annealing once the genome is uncoated, since both strands of viral DNA are packaged, but in separate virions (13). Presumably such annealing would be promoted by higher MOIs. Integration of the wild-type AAV genome appears to be mediated by the Rep proteins. Rep p78 and $p^{68}$ bind to the inverted terminal repeats (ITR) as well as to a specific site on chromosome 19 with sequence specificity thereby initiating integration of the AAV genome (38,39). In the absence of Rep, AAV appears to integrate at random (22).

In the following experiments, the high MOI required to achieve consistent integration of the rAAV genome may reflect several factors. First, viral entry into cells with low receptor numbers may be enhanced at high MOI. Second, the number of viral particles that actually enter the cell may be increased as a function of MOI and enhance the probability of annealing of the single stranded forms to create a double stranded template. Third, the amount of double stranded template may be relevant to the frequency of genome integration. Finally, we cannot exclude the presence of trace contaminants of adenovirus or AAV Rep proteins, even in these highly purified rAAV preparations. Such "contaminants" could influence the behavior of vectors by facilitating viral uptake or influencing the fate of the rAAV genome once within the target cell. Indeed, the MOI of greater than $10^7$ required for globin gene expression in transduced progenitor derived colonies in these experiments compared to the MOI of $10^3$ at which a proportion of progenitors were transduced with crude preparations (25) might reflect variable amounts of functional AAV and/or adenoviral proteins in the two preparations.

Persistence of the viral genome in an episomal state for variable periods of time following cell transduction temporally extends the opportunity for genomic integration. Repopulating stem cells are usually quiescent when purified from hematopoietic tissues but are thought to begin to proliferate when reinfused into a myeloablated recipient. Transduction of stem cells with rAAV can be accomplished ex vivo, creating the opportunity for subsequent integration as bone marrow regeneration is initiated.

The present invention is more particularly described in the following examples which are intended as illustrative only since numerous modifications and variations therein will be apparent to those skilled in the art.

EXAMPLE 1

Transduction of erythroid cells

MATERIALS AND METHODS

Vector Preparation: Two rAAV vectors were used. Each contained a human γ globin gene that had been mutationally marked by a six base pair deletion in its 5'untranslated region to allow its transcript to be measured in the presence of normal human γ globin mRNA. The first vector, rHS432$^A$γ* which contains three core hypersensitive sites from the LCR, has been previously described (25). Briefly, the human β-globin LCR fragments HS4, HS3, HS2 and the $^A$γ* globin gene were subcloned into a pUC007, and a Bgl II/Sal I fragment of this construct was subcloned into pUC008, which was then digested with Nhe I and ligated to the Xba I fragment of pSUB201. This plasmid construct (pJM24/vHS432$^A$γ*) was cotransfected with the complementing plasmid, pAAV/ad into 293 cells previously infected with adenovirus type 5 to make this rAAV, rHS432$^A$γ*. The second vector, rHS32$^A$γ*3'RE was derived from rHS432$^A$γ* by removing the site 4 LCR fragment and adding a 750 base pair EcoRI-HindIII fragment from downstream of the human $^A$γ globin gene that contains a regulatory element (RE) that associates with the nuclear matrix (29). Preparation of each of these rAAV vectors, using the cognate plasmids as substrates, was by modification of previously published methods (19,30). Purification was accomplished by buoyant density centrifugation in $CsCl_2$. The vector preparations had rAAV particle titers of $3-5\times10^{13}$/ml as determined by slot blot hybridization (25,28) and contained less than 0.01% contamination with adenovirus, also determined by slot blot analysis. Electron microscopy was used to verify that the preparations were free of adenovirus or cellular contaminants (28).

Cell Culture: Human erythroleukemia (K562) cells (31) were cultured in Improved Modified Eagles Medium (IMEM) containing 10% Fetal Calf Serum (FCS). Human hematopoietic progenitors were purified by positive selection for CD34 expression by antibody affinity purification (32, Ceprate Stem Cell Concentrator, Cell Pro, Inc., Bothwell, Wash.). Transduction was performed by exposing $10^5$ cells to rAAV in 2 ml of serum-free IMEM for 14–16 hours at 37° C. in 5% $CO_2$ with gentle, continuous rocking (25). Stem cell factor (100 ng/ml), interleukin-3 (20 ng/dl), and interleukin-6 (50 ng/ml) were added during transduction of CD34$^+$ cells. After transduction, the cells were washed in IMEM containing 10% FCS and plated in semi-solid medium containing methylcellulose (MethoCult™ GF—Terry Fox Laboratories, Vancouver, British Columbia). After 14–16 days, individual erythroid cell colonies were plucked from the cultures with a micro pipette and processed for RNA extraction. K562 cell colonies were placed in suspension culture in DMEM containing 10% FCS and RNA or DNA was extracted from an aliquot after culture for periods ranging from 2 days to several weeks. K562 cells were induced to undergo erythroid differentiation over 3 days by addition of 40 mM hemin as monitored by benzidine staining.

Nucleic Acid Analysis: RNA was recovered from individual primary erythroid colonies or K562 cells using RNA STAT-60 (Tel-Test Inc., Friendswood, Tex.) and concentrated by ethanol precipitation. Detection and semi-quantitation of nRNA species was by reverse transcriptase-polymerase chain reaction (RT-PCR) methodology using reagents provided by the manufacturer (Promega, Madison, Wis. and primers specific for β-actin, wild-type γ globin MRNA or the mutant human γ globin mRNA species. The conditions for RT-PCR analysis were as follows: 1) β-actin-25 cycles; 1 min. at 94°, 1 min. at 60°, 1 min. at 72° or 2) globin mRNAs- 25–30 cycles; 1 min at 94°, 1 min. at 60°, and 1 min. at 72°. The sequence of the β-actin primers were as follows: 5' GATGATATCGCCGCGCTCGT (SEQ ID NO: 1) and 5' GGTCATCTTCTCGCGGTTGG (SE ID NO: 2). The sequences of the globin MRNA specific primers have already been published (25). The PCR products were resolved on a polyacrylamide gel (Protogel, National Diagnostics, Atlanta, Ga.) and quantitated using a phospho-imager (molecular Dynamics, Sunnyvale, Calif.). DNA was extracted from K562 cells using standard methods and analyzed by Southern blot methodology (33) using a 900 base pair EcoRI-BamHI fragment containing intron II of the human $^A$γ globin gene as a probe.

Fluorescence in situ Hybridization: Genomic DNA subcloned into vectors was nick-translated with digoxigenin-11-UTP and hybridized overnight at 37° C. to fixed metaphase chromosomes according to the method of (85), except for the inclusion of 500 µg/ml of highly reiterated human DNA self-annealed to Cot 1 (Bethesda Research Laboratories, Gaithersburg, Md.). Signals were detected by incubating the slides with fluorescein-conjugated sheep anti-digoxigenin antibodies (Boehringer Mannhein, Indianapolis, Ind.) followed by counterstaining in 4,6-diamidino-2-phenylindole (DAPI). Fluorescence microscopy was performed with a Zeiss standard microscope equipped with fluorescein epifluorescence filters.

RESULTS

Figure 1B:
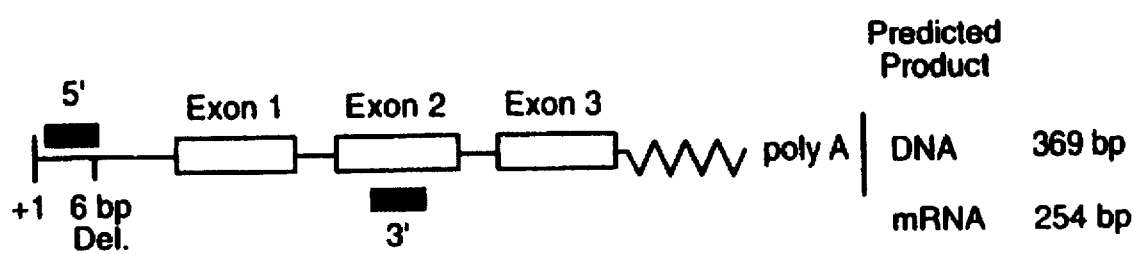

Multiplicity of Infection Required for Transduction of Erythroid Progenitors: The availability of concentrated, highly purified rHS432$^A\gamma^*$ permitted a precise titration of the ratio of vector particles to target cells required for introduction of the vector genome into primary clonogenic progenitors. Enriched CD34$^+$ bone marrow cells (50–80% pure) were exposed to various multiplicities of infection (MOI) and cultured in semi-solid medium. Individual erythroid colonies were plucked from the culture after 14–16 days of incubation and RNA recovered for analysis. At an MOI of $1.4\times10^7$, zero of eleven colonies contained the $^A\gamma^*$ transcript whereas at MOI's of $7.5\times10^7$ and $3.0\times10^8$, nine of eleven and seventeen of twenty-two colonies contained the $^A\gamma^*$ transcript, respectively FIG. 1 and data not shown). These data substantiate our earlier observations regarding the ability of rAAV to introduce and express a globin gene in primary erythroid progenitors (25) and establish that with highly purified preparations, a very high MOI is required for this purpose.

Figure 2:
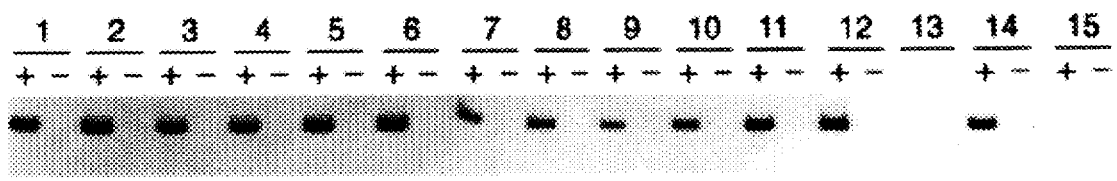
FIG. 2 shows detection of the rAAV encoded transcript in erythroleukemia (K562) cell colonies. Erythroleukemia cells were transduced with rHS432$^A$γ* at an MOI of 3×10$^8$, cultured in semi-solid medium for 14 days after which individual colonies were plucked, expanded for 1–2 days in liquid medium and an aliquot of the cells used for RNA extraction. Lanes 1–12: RT-PCR analysis to detect the $^A$γ* transcript; (+) is with reverse transcriptase and (−) is the control without reverse transcriptase. Lane 13: "Water" blank for the PCR reaction. Lane 14: RNA extracted from a cell line containing a single integrated copy of the $^A$γ* gene linked to HS2. Lane 15: RNA from control K562 cells that had not been transduced.
Figure 3A:
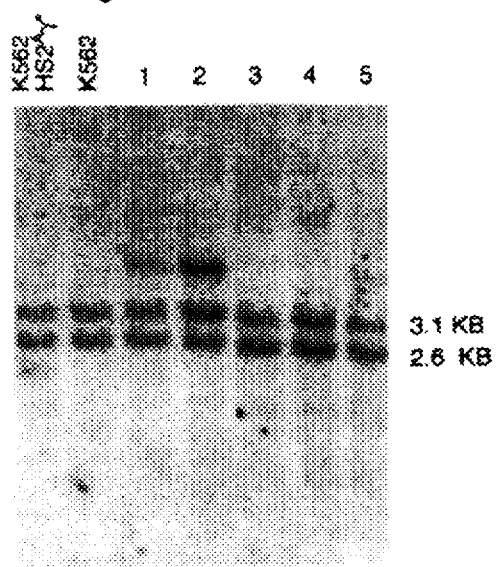
FIGS. 3A–3B show genomic integration of the rHS432$^A$γ* genome. Individual clones, derived from K562 cells transduced at a MOI of 3×10$^8$, were cultured in semi-solid medium for 14 days and then expanded in liquid culture for 3–4 weeks. DNA was extracted and analyzed by the Southern blot methodology after restriction with EcoR1 and BglII (A) or StuI (13). DNA extracted from a cell line containing a single integrated copy of a rAAV genome that includes the $^A$γ* gene K562 HS2$^A$γ*) served as a positive control (left lane) whereas K562 cells provided DNA which served as a negative control (second lane from left). The bands of 2.6 and 3.1 kb (A) or the 4.0 and 4.9kb bands (B) present in each lane contain the endogenous γ globin genes. The diagram below indicates the organization of the rAAV vector genome and the location of specific restriction endonuclease sites. EcoR1 and BglII (A) release an internal rAAV band of 4.4 kb whereas StuI releases a junction fragment of variable length that includes a portion of the rAAV genome and human chromosomal DNA.
Figure 3B:
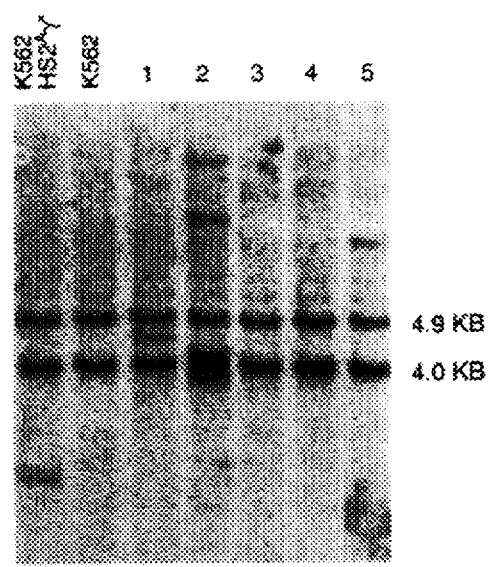
Figure 3C:
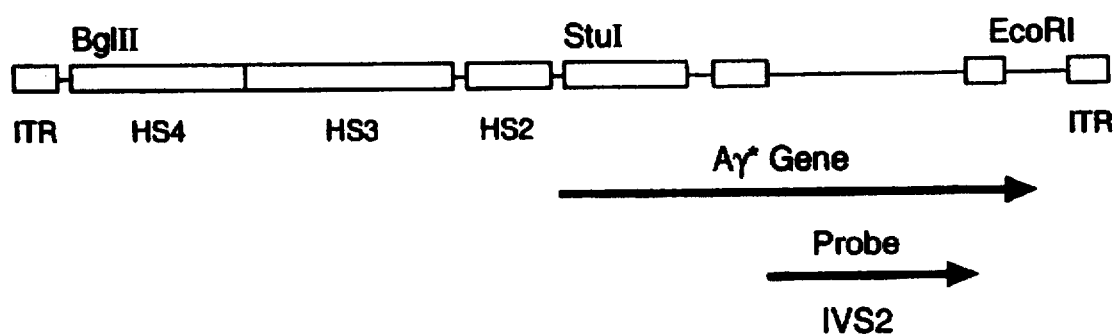
Figure 4A:
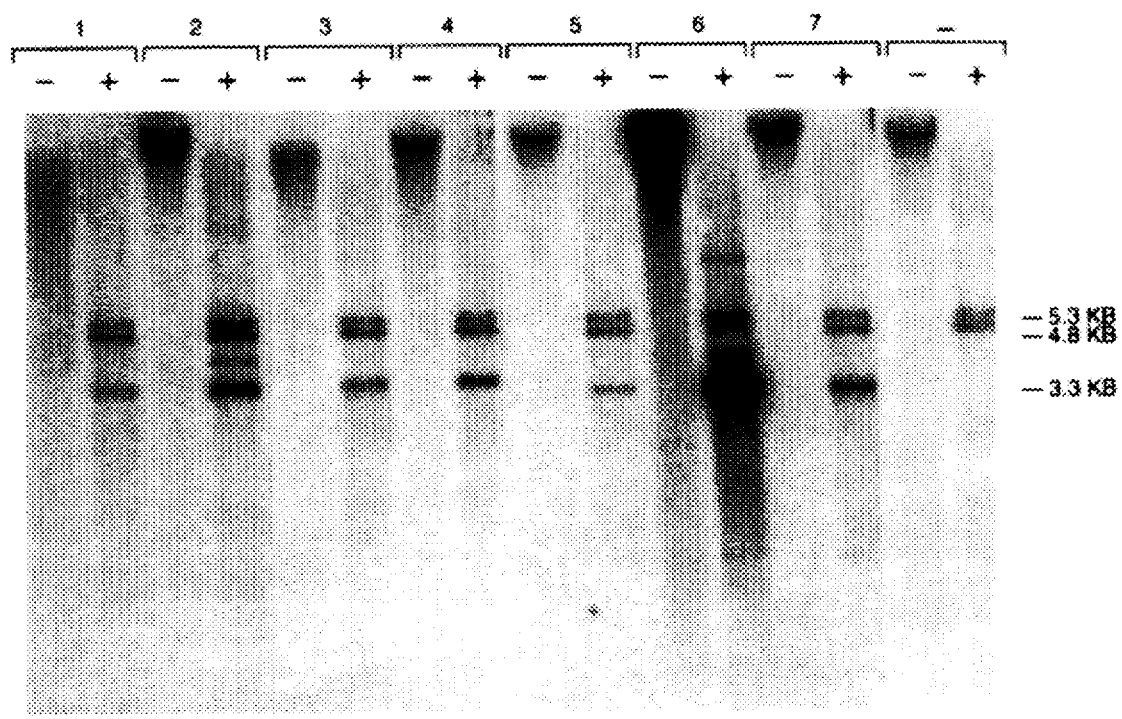
FIGS. 4A–4C show genomic integration of the rHS32$^A$γ*3'RE genome. Individual colonies of K562 cells, transduced at a MOI of 4×10$^9$, were cultured in semi-solid medium for 14 days and then expanded in liquid culture for 2–4 weeks. A: DNA from seven individual colonies analyzed without restriction (−) or cut with BsaBI (+). The bands at 4.8 and 5.3 kb contain the endogenous globin genes whereas the band at 3.3 kb is a internal fragment derived from the vector genome (see diagram below). The negative control lanes contain DNA derived from non-transduced K562 cells. B and C: DNA from the same seven colonies and the negative control restricted with StuI or EcoRI, respectively. StuI releases variable length junction fragments, a 4.7 kb band derived from head to tail concatamers of the rAAV genome and 4.0 and 4.9 kb fragments containing the endogenous globin genes. EcoRI releases a 3.4 kb fragment derived from tandem repeats of the rAAV genome, variable length junction fragments and two fragments of 2.6 and 3.1 kb containing the endogenous γ globin genes.
Figure 4B:
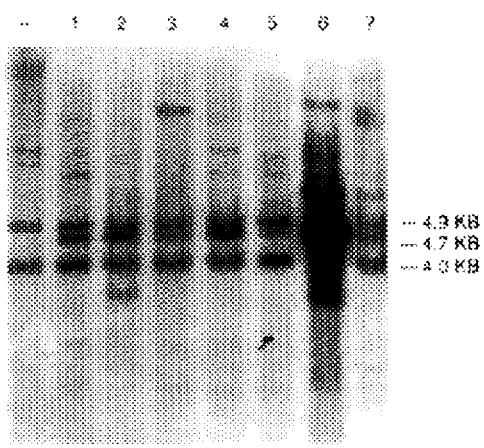
Figure 4C:
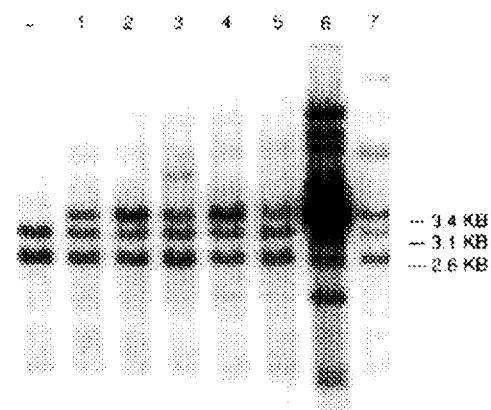
Figure 4D:
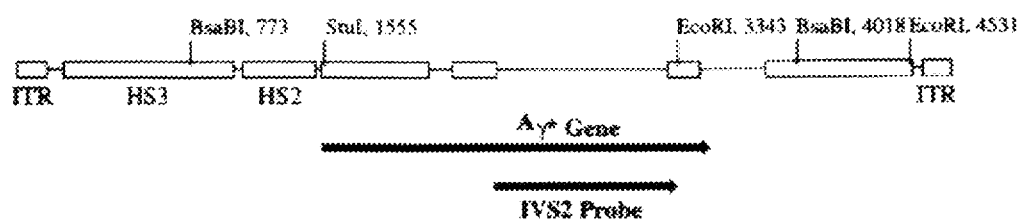

Prolonged Expression of the rHS432$^A\gamma^*$ Globin Gene Without Genomic Integration: The limited proliferative potential of primary clonogenic erythroid progenitors precludes attempts to investigate the relationship between viral uptake and initial gene expression and subsequent genomic integration. To study this relationship, we used human erythroleukemia (K562) cells (31) as a model. K562 cells were transduced with rHS432$^A\gamma^*$ at a MOI of $3\times10^8$, plated in semi-solid medium and incubated for 17 days after which individual clones were plucked and transferred to liquid culture. Twenty-four hours later RNA was extracted from an aliquot of the cells. All transduced colonies analyzed were found to contain the $^A\gamma^*$ globin MRNA transcript FIG. 2 and Table I). Seventeen days later a second aliquot was analyzed; the cells from nineteen of twenty-three clones studied contain the $^A\gamma^*$ globin mRNA (Table I). However, only nine of sixteen clones studied contain an integrated vector genome on Southern blot analysis and in only five of these was the genome unrearranged. Representative results are shown in FIG. 3. Restriction with EcoRI and BglII released the predicted 4.4 kilobase unrearranged genomic fragment in DNA from three of five clones: in one of these clones (2) the intensity of the vector band suggested the presence of multiple integrated copies. Digestion with StuI which cuts once in the vector genome releases a junction fragment, the length of which is a characteristic of the integration site. Clones 1 and 5 contain a single integrated provirus whereas clone 2 contains at least 4 genomic copies each of which appears to be integrated at a separate chromosomal location (FIG. 3).

RNA extracted from clones 1 and 5 after an additional four weeks of exponential growth in culture was found to contain the $^A\gamma^*$ transcript at concentrations approximately equivalent to 7 or 9%, respectively, of the mRNA species encoded by the endogenous γ-globin genes. After correction for relative copy number (6 endogenous versus one 1 transduced), the rAAV encoded globin gene appeared to be expressed at 42 or 54%, respectively, of the level of each endogenous gene. Clone 2 contained a high level of the $^A\gamma^*$ transcript, consistent with presence of the multiple integrated copies of the rAAV genome in this cell line.

Expression of the γ globin gene from an episomal rAAV genome has now been documented in that we found consistent expression in all transduced clones, 50% or fewer of which were subsequently found to contain the vector genome on Southern blot analysis of genomic DNA FIG. 3 and Table I).

TABLE 1 rAAV Mediated Globin Gene Transfer into Erythroleukemia (K562) Cells

| | | mRNA (RT-PCR) | | Integration (SOUTHERN BLOT) | | |
|---|---|---|---|---|---|---|
| | MOI | Day 18 | Day 35 | Integrated | Unrearranged | Tandem Copies |
| rHS432$^A\gamma^*$ | $3\times10^8$ | 12/12* | 19/23* | 9/16* | 5/9* | 0/9* |
| rHS32$^A\gamma^*$3'RE | $4\times10^8$ | 10/10 | ND | 8/18 | 8/8 | 6/8 |
| rHS32$^A\gamma^*$3'RE | $4\times10^9$ | 10/10 | ND | 23/24 | 23/23 | 22/23 |

*Ratio of positive clones to number of clones analyzed.
Southern blot analysis was performed on DNA extracted 35 to 50 days after transduction.

Integration of rHS32$^A\gamma^*$3'RE as a Tandem Array of Head to Tail Copies: A second vector, rHS32$^A\gamma^*$3'RE, was created to further evaluate the potential of rAAV to mediate genomic integration and persistent globin gene expression. The regulatory element downstream from the genomic $^A\gamma^*$ globin gene was added in an effort to determine its effect on vector stability, integration and gene expression, and the site 4 LCR fragment of HS enhancer element was removed to create more room in the vector, evidence that it is not critical for LCR function in mouse. Again, all K562 clones studied 18 days post-transduction contained the $^A\gamma^*$ globin PRNA species (Table I). Eight of eighteen clones derived from cells transduced at a MOI of $4\times10^8$ contained an intact vector genome whereas twenty-three of twenty-four clones derived from cells transduced at a MOI of $4\times10^9$ contained the vector genome (FIG. 4 and Table I).

Southern blot analysis confirmed that the vector genome was integrated in all clones in which it was present (FIG. 4 and data not shown). Analysis of uncut genomic DNA indicated that all hybridizing sequences migrated with high molecular weight DNA. Restriction with an enzyme (BsaBI) which cuts twice in the vector genome released the internal band of predicted length in every case; the signal intensity of this band suggested variable copy number among the clones. Six clones contained in addition a rearranged genome as reflected by a BsaBI band that deviated in length from that predicted. Restriction with StuI, an enzyme that cuts once in the vector genome, released a genomic length band of 4.7 kb DNA from the vast majority of clones that contained an integrated vector genome (22 of 23 clones, Table 1). This band suggests the presence of head to tail concatamers arranged in a tandem array. The copy number of the tandem array was estimated by comparing the signal of the internal BsaBI band derived from the rAAV genome to the combined signal of the two BsaBI bands containing the endogenous γ globin genes (FIG. 4). Three clones had very high estimated copy numbers of 25, 55 and 124 whereas in the remaining nineteen, the copy number ranged from 3 to 14 with a median of 6. Restriction with EcoRI, an enzyme which cuts twice in the vector genome, yielded the 3.4 kb fragment predicted from the presence of such a tandem array. In addition, StuI and EcoRI yielded one or more hybridizing fragments of variable length in each clone; these are the junction fragments between genomic DNA and integrated copies of the vector genome.

Figure 5:
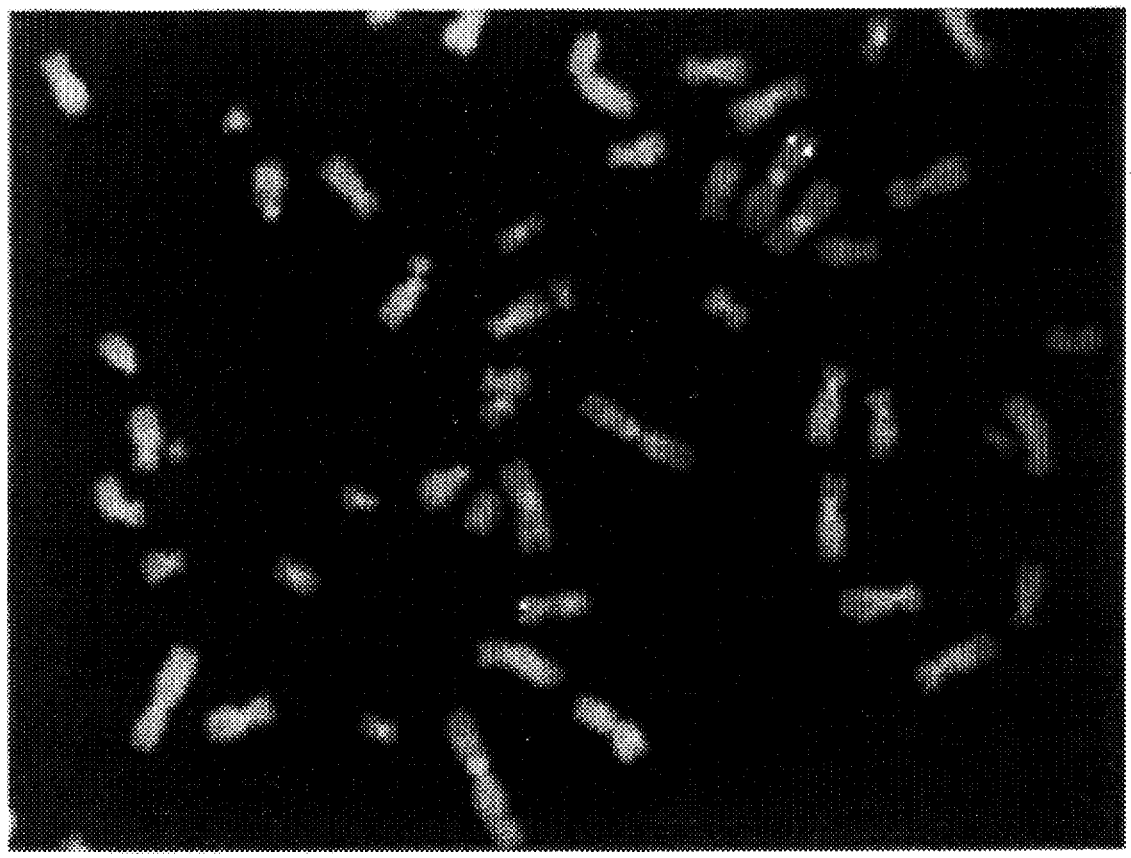
FIG. 5 shows fluorescence in situ hybridization (FISH) analysis of a clone transduced with rHS32$^A$γ*3'RE. A signal is present on chromosome 11 p15 (small chromosome above), the position of the normal β-like globin gene locus, and at chromosome 2q37 (large chromosome below), the position of the integrated rAAV genome in this cell line.

Fluorescence in situ hybridization (FISH) was performed on several clones to verify genomic integration of the vector sequences. The genomic locus of the γ-globin gene was detected at 11p15 in all clones studied. In addition, one cell line contained a clonal integration site at 1q, a second cell line contained a clonal integration site at 2q37 (FIG. 5) as well as several other nonclonal sites, and a third cell line contained several random, nonclonal sites of integration. The presence of nonclonal sites in cells from a single colony is consistent with delayed integration of the vector genome following initiation of proliferation of a transduced cell. To test this hypothesis, several subclones of cell line 14 were studied. Three contained a clonal integration site on 1q, one contained a clonal integration site at the centromer of an unidentified chromosome and another contained a clonal integration site at 2q37.

Figure 6:
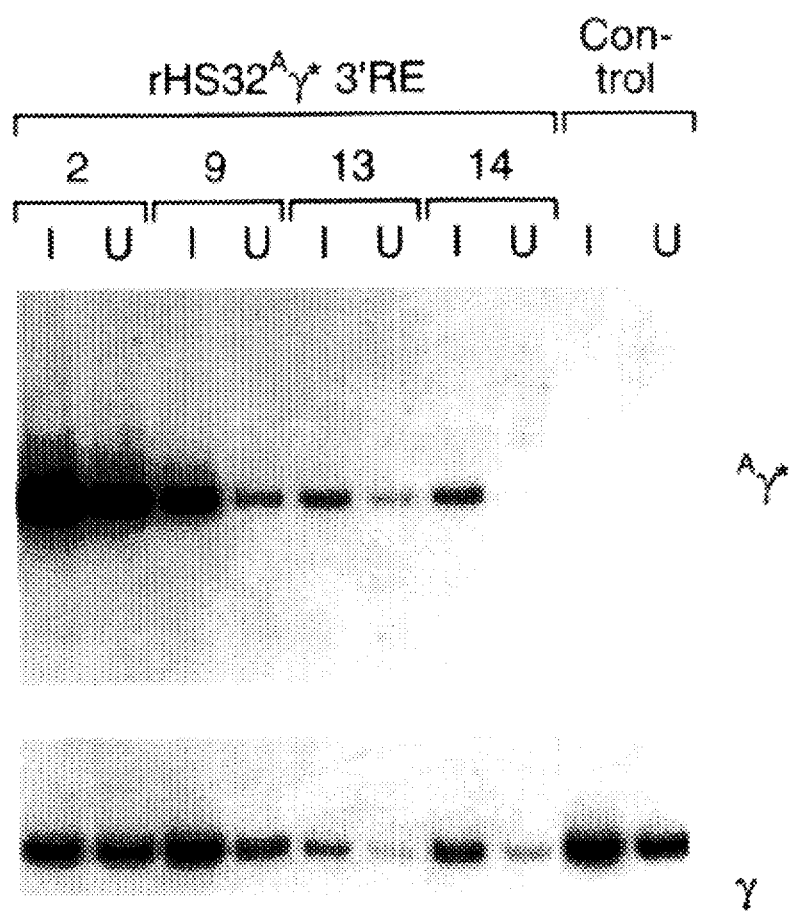
FIG. 6 shows expression of the $^A$γ* gene in cells containing a tandem array of the rHS32$^A$γ*3'RE genome. RNA was extracted from four clones after passage for 4–6 weeks in culture. Samples were extracted from uninduced (U) cells and those induced (I) by culture for three days in 40 mM hemin. Clone 2 was derived from cells transduced at an MOI of $4 \times 10^8$ and contains 65 integrated copies of the rHS32$^A$γ*3'RE genome whereas clones 9, 13 and 14 were derived from cells transduced at an MOI of $4 \times 10^9$ and contain 5, 3 and 4 copies, respectively. The conditions for PCR and signal detection were identical for the analysis specific for the γ and $^A$γ* MRNA species, permitting direct comparison of signal intensity with respect to mRNA concentration.

Expression of the rAAV encoded globin genes was evaluated by semi quantitative RT-PCR. The $^A\gamma^*$ globin gene was inducible and expressed at levels that varied from 40 to 100% that of an endogenous γ globin gene when corrected for gene copy number (FIG. 6).

Thus, a vector containing hypersensitive sites 2 and 3 from the locus control region (LCR) and the regulatory element from 3' to the $^A\gamma$ globin gene integrated with highest efficiency, creating tandem head to tail arrays usually composed of 3 to 14 copies of the intact rAAV genome in each clonal cell population. Expression of the rAAV encoded globin gene was at levels comparable to that of an endogenous γ globin gene at its native chromosomal location.

EXAMPLE 2

Transduction of Hematopoietic Stem Cells with Globin Gene rHS32$^A\gamma$*3RE is prepared as described in Example 1. Bone marrow and peripheral blood samples are obtained and albumin gradient separation used to isolate a mononuclear cell fraction. The mononuclear cells are processed on a stem cell concentrator (CellPro.Inc., Bothell, Wash.) according to manufacturer's directions to obtain a CD34-enriched population of progenitor and stem cells.

CD34-enriched bone marrow and/or peripheral blood cells are transduced using clinical grade virus preparations at a MOI of $10^2$ to $10^9$ for a maximum of 72 hours at 37° C. in 5% $CO_2$. Cultures are supplemented with $^4$ µg/ml protamine sulphate (Elkins-Sinn, Cherry Hill, N.J.), 20 ng/ml interleukin-3 (IL-3, Sandoz, East Hanover, N.J.), 100 ng/ml stem cell factor (Amgen, Thousand Oaks, Calif.) and 50 mg/ml gentamycin sulfate (GIBCO, Gaithersburg, Md.). Every 24 hours, cells are centrifuged and resuspended in fresh viral supernatant, protamine and growth factors. At the end of the incubation period, both nonadherent and adherent (by standard trypsin dislodgment) cells are harvested. Cells can be assessed for viability, CD34 expression, etc. An aliquot of cells is retained for transduction efficiency assessment by the method set forth in Example I. The remainder of the cells can be cryopreserved until transfusion.

The cells are infused back into the patient by the method described in Dunbar et al., (5), and as follows. If frozen, cells are rapidly thawed in a 37° C. water bath and rapidly infused through a central venous catheter. The subject is allowed to recover while vital signs are monitored. Post-transfusion, hydration and alimentation are monitored to insure they are adequate. The subject is also monitored to manage infection.

To transduce hematopoietic cells with another gene of interest, the globin gene of rHS32$^A\gamma$*3'RE is replaced with the gene of interest by standard recombinant methods. The method described in this example is then performed.

EXAMPLE 3

Direct provision of a functional nucleic acid to cells of a subject

Vectors are prepared as set forth in Example 1. If a gene other than human $^A\gamma$ globin is of interest, the γ globin gene of rHS32$^A\gamma$*3'RE is replaced with the gene of interest using standard recombinant DNA techniques. For example, the gene encoding the CFTR protein could be inserted.

The vectors are then administered to the patient by a route that presents the vector to the desired target. rHS32$^A\gamma$*3'RE can be directly administered to the blood by intravenous injection. The vector can be directly administered to the target organ by direct injection into the target organ, by standard methods. The vector can also be directly injected into the CNS. To administer to the lungs, the vector can be inhaled or injected intratracheally. For example, the vector containing a CFTR insert could be placed in phosphate buffered saline, nebulized and inhaled by the patient to deliver the vector to the lung where the CFTR is expressed.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof it is not intended that such details should be regarded as limitations upon the scope of the invention except as and to the extent that they are included in the accompanying claims.

REFERENCES

1. Crystal R. G.: Transfer of genes to humans: early lessons and obstacles to success. Science 270: 404, 1995

2. Dunbar C. E., Emmons R. V.: Gene transfer into hematopoietic progenitor and stem cells: progress and problems. Stem Cells 12: 563, 1994

3. Walsh C. E., Liu J. M., Miller J. L., Nienhuis A. W., Samulski R. J.: Gene therapy for human hemoglobinopathies. Proc Soc Exp Biol Med 204: 289, 1993

4. Brenner M. K., Rill D. R., Moen R. C., Krance R. A., Mirro J. Jr, Anderson W. F., Ihle J. N.: Gene-marking to trace origin of relapse after autologous bone-marrow transplantation. Lancet 341: 85, 1993

5. Dunbar C. E., Cottler-Fox M, O'Shaughnessy J. A., Doren S., Carter C., Berenson R., Brown S., Moen R. C., Greenblatt J., Stewart F. M., Leitman S. F., Wilson W. H., Cowan K., Young N. S., Nienhuis A. W.: Retrovirally marked, CD34-enriched peripheral blood and bone marrow cells contribute to long-term engraftment after autologous transplantation. Blood 85: 3048, 1995

6. Dzierzak E. A., Papayannapoulou T., Mulligan R. C.: Lineage-specific expression of a human beta-globin 7. Chang J. C., Liu D., Kan Y. W.: A 36-base-pair core sequence of locus control region enhances retrovirally transferred human beta-globin gene expression. Proc Natl Acad Sci USA 89:3107, 1992

8. Plavec I., Papayannopoulou T., Maury C., Meyer F.: A human beta-globin gene fused to the human beta-globin locus control region is expressed at high levels in erythroid cells of mice following engraftment with retrovirus-transduced hematopoietic stem cells. Blood 81: 1384, 1993

9. Leboulch P., Huang G. M., Humphries R. K., Oh Y. H., Eaves C. J., Tuan D. Y., London I. M.: Mutagenesis of retroviral vectors transducing human beta-globin gene and beta-globin locus control region derivatives results in stable transmission of an active transcriptional structure. EMBO J 12: 3065, 1994

10. Takekoshi K. J., Oh Y. I., Westerman K. W., London I. M., Leboulch P.: Retroviral transfer of a human beta-globin/delta-globin hybrid gene linked to the beta locus control region hypersensitive site 2 aimed at the gene therapy of sickle cell disease. Proc Natl Acad Sci USA 92: 3014, 1995

11. Sadelain A., Wang C. R. L. Antoniou M., Grosveld F., Mulligan R. C.: Generation of a high-titer retroviral vector capable of expressing high levels of the human beta-globin gene. Proc Natl Acad Sci USA 92: 6728, 1995

12. McCune S. L., Townes T. M.: Retroviral vector sequences inhibit human beta-globin gene expression in transgenic mice. Nucleic Acids Res 22: 4477, 1994

13. Muzyczka N.: Use of adeno-associated virus as a general transduction vector for mammalian cells. Curr Top Microbiol Immunol 158: 97, 1992

14. Kotin R. M.: Prospects for use of adeno-associated virus as a vector for human gene therapy. Hum Gene Ther 5: 793, 1994

15. Flotte T. R., Carter B. J.: Adeno-associated virus vectors for gene therapy. Gene Ther2: 357, 1995

16. Relling F., Samulski R. J.: AAV as a viral vector for gene therapy. Mol Biotech 3: 9, 1995

17. Kotin R. M., Siniscalco M., Samulski R. J., Zhu X., Hunter L., Laughlin C. A., McLaughlin S., Muzyczka M., Rocchi M., Berns K. I.: Site-specific integration by adeno-associated virus. Proc Natl Acad Sci USA 87: 2211, 1990

18. Samulski R. J., Zhu X., Xiao X., Brook J. D., Housman D. E., Epstein N., Hunter L. A.: Targeted integration of adeno-associated virus (AAV) into human chromosome 19. EMBO J 10: 3941, 1991

19. Chiorini J. A., Wendtner C. M., Urcelay E., Safer B., Hallek M., Kotin R. M.: High-efficiency transfer of the T-cell co-stimulatory molecule B7-2 to lymphoid cells using high-titer recombinant adeno-associated virus vectors. Hum Gene Ther6: 1531, 1995

20. Clark K. R., Voulgaropoulou F., Fraley D. M., Johnson P. R.: Cell lines for the production of recombinant adeno-associated virus. Hum Gene Ther 6: 1329, 1995

21. Tamayose K., Hirai Y., Shimada T.: A new strategy for large scale preparation of high titer recombinant adeno-associated virus (AAV) vectors by using packaging cell lines and sulfonated cellulose column chromatography. Hum Gene Ther, In press.

22. Walsh C. E., Liu J. K., Xiao X., Young N. S., Nienhuis A. W., Samulski R. J.: Regulated high level expression of a human gamma-globin gene introduced into erythroid cells by an adeno-associated virus vector. Proc Natl Acad Sci USA 89: 72571992

23. Miller J. L. et al: Single-copy transduction and expression of human γ-globin in K562 erythroleukemia cells using recombinant adeno-associated virus vectors: the effect of mutations in NF-E2 and GATA-1 binding motifs within the hypersensitivity site 2 enhancer. Blood 82: 1900, 1993

24. Einerhand M. P. W., Antoniou M., Zolotukhin S., Muzyczka N., Berns K. I., Grosveld F., Valerio D.: Regulated high-level human P-globin gene expression in erythroid cells following recombinant adeno-associated virus-mediated gene transfer. Gene Ther 2: 336, 1995

25. Miller J. L., Donahue R. E., Sellers S. E., Samulski R. J., Young N. S., Nienhuis A. W.: Recombinant adeno-associated virus (rAAV) mediated expression of a human γ-globin gene in human progenitor derived erythroid cells. Proc Natl Acad Sci USA 91: 10183, 1994

26. McLaughlin S. K., Collis P., Hermonat P. L., Muzyczka N.: Adeno-associated virus as general transduction vectors: analysis of proviral structures. J Virol 62: 1963, 1988

27. Fisher K. J., Cao G.-P., Weitzman M. D., DeMatteo R., Burda J. F., Wilson J. M.: Transduction with recombinant adeno-associated virus for gene therapy is limited by leading-strand synthesis. J Virol 70: 520, 1996

28. Bertran J., Miller J. L., Yang Y., Fenimore A. K., Rueda F., Vanin E. F., Nienhuis A. W.: Recombinant Adeno-Associated Virus (rAAV) Mediated High Efficiency, Transient Expression of the Murine Cationic Amino Acid Transporter (Ecotropic Retroviral Receptor) Permits Stable Transduction of Human HeLa Cells by Ecotropic Retroviral Vectors. J Virol Accepted for publication pending revisions.

29. Cunningham J. E. K. Purucker M. E., Jane S. M., Safer B., Vanin E. F., Ney P. A., Lowrey C. H., Nienhuis A. W.: The regulatory element 3' to the A gamma-globin gene binds to the nuclear matrix and interacts with special A-T-rich binding protein 1 (SATB1), an SAR/MAR-associating region DNA binding protein. Blood 84: 1298, 1994

30. Samulski R. J., Chang L. S., Shenk T.: Helper-free stocks of recombinant adeno-associated viruses: normal integration does not require viral gene expression. J Virol 63: 3822, 1989

31. Lozzio C. B., Lozzio B. B.: Human chronic myelogenous leukemia cell-line with positive Philadelphia chromosome. Blood 45: 321, 1975

32. Bensinger W. I., Bereson R. J., Andrews R. G., Kalamasz D. F., Hill R. S., Bernstein I. D., Lopez J. G., Buckner C. D., Thomas E. D.: Positive selection of hematopoietic progenitors from marrow and peripheral blood for transplantation. J Clin Apheresis 5: 74, 1990

33. Sambrook J., Fritsch E. F., Maniatis T.: Molecular cloning: a laboratory manual. Cold Spring Harbor, New York, Cold Spring Harbor Laboratory, 1989

34. Albritton L. M., Kim J. W., Tseng L., Cunningham J. M.: Envelope-binding domain in the cationic amino acid transporter determines the host range of ecotropic murine retroviruses. J Virol 67: 2091, 1993

35. Russell D. W., Alexander I. E., Miller A. D.: DNA synthesis and topoisomerase inhibitors increase transduction by adeno-associated virus vectors. Proc Natl Acad Sci USA 92: 5719, 1995

36. Russell D. W., Miller A. D., Alexander I. E.: Adeno-associated virus vectors preferentially transduce cells in S phase. Proc Natl Acad Sci USA 91: 8915, 1994

37. Halbert C. L., Alexander I. E., Wolgamot G. M., Miller A. D.: Adeno-associated virus vectors transduce primary cells much less efficiently than immortalized cells. J Virol 69: 1473, 1995

38. Weitzman M. D., Kyostio S. R., Kotin R. M., Owens R. A.: Adeno-associated virus (AAV) Rep proteins mediate complex formation between AAV DNA and its integration site in human DNA. Proc Natl Acad Sci USA 91: 5808, 1994

39. Chiorini J. A., Yang L., Safer B., Kotin R. M.: Determination of adeno-associated virus Rep68 and Rep78 binding sites by random sequence oligonucleotide selection. J Virol 69:7334, 1995

40. Dick J. E.: Future prospects for animal models created by transplanting human haematopoietic cells into immune-deficient mice. Res Immunol 145: 380, 1994

41. Bock T. A., Orlic D., Dunbar C. E., Broxmeyer H. E., Bodine D. M.: Improved engraftment of human hematopoietic cells in severe combined immunodeficient (SCID) mice carrying human cytokine transgenes. J Exp Med 182: 2037, 1995

42. Jarman and Higgs *EMBO J* 7:3337 (1988)

43. Laemmli et al., *Curr. Opin. Genet Dev.* 2:275 (1992)

44. Bode et al., *Science* 255:195 (1992)

45. Stief et al, *Nature* 341:343 (1989)

46. Hofmann et al., *Cell* 57:725 (1989)

47. Bodine and Ley, *EMBO J* 6(10):2997–3004 (1987)

48. Jarman and Higgs *EMBO J* 7:3337 (1988)

49. Zong and Scheuermann, *J Biol. Chem.* 270(41):24010–24018 (1995)

50. Avramova et al., *Plant Cell* 7(10):1667–1680 (1995)

51. Chong et al., *Biochim. Biophys. Acta* 1264(1):103–114 (1995)

52. Balasubramaniam and Oleinick *Biochemistry* 34(39):12790–12802 (1995)

53. Rzeszowska-Wolny and Rogolinski, *Acta Biochim. Pol.*41(4):459–466 (1994)

54. Durfee, et al, *J Cell. Biol.* 127(3):609–622 (1994)

55. Hibino, et al., *Cancer Lett.* 88(1):49–55 (1995)

56. Zeng, et al., *Cell Motil. Cytoskeleton* 29(2):167–176 (1994)

57. Dickinson and Kohwi-Shigematsu, *Mol. Cell. Biol.* 15(1):456–465 (1995)

58. Boulikas, *J Cell. Biochem.* 55(4):513–529 (1994)

59. Forrester et al., *Science* 265 (5176):1221–1225 (1994)

60. Romig, et al., *Eur. J Biochem.* 221(1):411–419 (1994)

61. Betz, et al., *Cell* 77(2):239–248 (1994)

62. Nakagomi, et al., *Mol. Cell. Biol* 14(3):1852–1860 (1994)

63. Das et al., *Eur. J Biochem,* 215(3):777–785 (1993)

64. Boulikas, *J Cell. Biochem.* 52(1): 23–36 (1993)

65. Fishel et al., *Proc. Natl. Acad Sci. USA* 90(12):5623–5627(1993)

66. Bidwell et al. *Proc. Natl. Acad. Sci. USA* 90(8):3162–3166 (1993)

67. Boulikas *J Cell. Biochem.* 52(1):14–22 (1993)

68. Lieberson et al. *EMBO J* 14(24):6229–6238 (1995)

69. Benecke et al. *Diabetes* 42(1):206–212 (1993)

70. Jones et al.,

71. Simonet et al. *J Biol. Chem.* 268(11):8221–8229 (1993)

72. Bernier et al. *Mol. Cell Biol.* 13(3):1619–1633 (1993)

73. Judd, *Genetics* 141(1):245–253 (1995)

74. Festenstein et al. *Science* 271(5252): 1123–1125 (1996)

75. Robinson W. E. Jr. and Mitchell W. M., *AIDS* 4:S151–S162(1990)

76. Goodman et al., *Blood* 84(5):1492–1500 (1994)

77. Bartlett and Samulski, Genetics and Biology of Adeno-Associated Virus in *Viral Vectors*, Academic Press, Inc. (1995)

78. Ferrari et al., *J Virol.*70(5):3227–3234 (1996)

79. Brenner, et al. *Human Gene Therapy* 2:137–159 (1991)

80. *Merritt's Book of Neurology*, 9th ed. L. P. Rowland, M. D.,ed.; Williams and Wilkins, Baltimore, 1995)

81. Brenner, et al. *Human Gene Therapy* 2:137–159 (1991)

82. Sopper et al., *Gene Ther.* 1(2):108–113 (1994)

83. Rando et al. *Exp. Cell. Res.* 220(2):383–389 (1995)

84. Mendell et al. *N. Engl. J Med.* 333(13): 871–873 (1995)

85. Pinkel, et al. *Proc. Natl. Acad. Sci. USA* 85:9138 (1988)

86. Dayhoff et al. (in *Atlas of Protein Sequence and Structure* 1978, Nat'l Biomed. Res. Found., Washington, D.C.)

87. WO 95/34670 (Johnson, P. R.)

88. Yao et al., *Gene Ther.* 1(2):99–107 (1994)

---

What is claimed is:

1. A vector for stable integration and long term expression of a nucleic acid comprising an enhancer element and a nuclear matrix association region inserted between an inverted terminal repeat of adeno-associated virus.

2. The vector of claim 1, further comprising a heterologous nucleic acid inserted into the vector.

3. The vector of claim 1, wherein the nuclear matrix association region comprises the 3' regulatory element of γ globin.

4. The vector of claim 2, wherein the nucleic acid encodes a globin.

5. The vector of claim 4, wherein the globin is γ globin.

6. The vector of claim 3, wherein a heterologous nucleic acid is inserted 5' of the 3' regulatory element of γ globin.

7. The vector of claim 1, wherein the enhancer element comprises a hypersensitive element of the globin gene cluster.

8. The vector of claim 7, wherein the hypersensitive element is HS3.

9. The vector of claim 7, wherein the hypersensitive element is HS2.

10. The vector of claim 7, where in the hypersensitive element comprises HS3 and HS2.

11. The vector of claim 1, wherein the vector further comprises a restriction endonuclease recognition site between the enhancer element and the nuclear matrix association region.

12. A particle containing the vector of claim 1.

13. A composition comprising the particle of claim 12.

14. An isolated cell containing the vector of claim 2.

15. A vector for stable integration and long term expression of a nucleic acid comprising a globin gene cluster hypersensitive element, the 3' regulatory element of γ globin, and a nucleic acid encoding a protein, each inserted between an inverted terminal repeat of adeno-associated virus such that the nucleic acid encoding the protein can be expressed.

16. The vector of claim 15, wherein the globin gene cluster hypersensitive element comprises HS3 and HS2.

17. The vector of claim 15, wherein the protein is globin.

18. The vector of claim 17, wherein the globin is γ globin.

19. The vector of claim 15, wherein the nucleic acid encoding a protein is inserted 5' of the 3' regulatory element.

20. A viral particle containing the vector of claim 15.

21. An isolated hematopoietic stem cell containing the viral particle of claim 20.

22. A vector for stable integration and long term expression of a protein comprising a globin gene cluster hypersensitive element, a 3' regulatory element of γ globin, and a nucleic acid encoding a protein, each inserted between an inverted terminal repeat of adeno-associated virus, wherein the nucleic acid encoding the protein is inserted 3' of the hypersensitive element and 5' of the 3' regulatory element.

23. The vector of claim 22, wherein the protein is globin.

24. The vector of claim 23, wherein the globin is γ globin.

25. A method for integration of a nucleic acid into the genome of a cell, comprising administering to the cell the vector of claim 2, thereby integrating the nucleic acid into the genome of the cell.

26. The method of claim 25, wherein the vector is administered at a high multiplicity of infection.

27. The method of claim 25, wherein the vector is administered in the absence of drug selection.

28. A method for integration of a globin gene into the genome in a cell, comprising administering to the cell the vector of claim 17, thereby integrating the globin gene into the genome in the cell.

29. The method of claim 28, wherein the cell is a hematopoietic stem cell.

30. The method of claim 28, wherein the vector is administered at a high multiplicity of infection.

31. The method of claim 26, wherein the vector is administered in the absence of drug selection.

32. A method of expressing a protein in a subject comprising administering to the subject a cell to which the vector of claim 22 has been administered ex vivo, thereby expressing the protein in the cell in the subject.

33. The method of claim 32, wherein the cell is a hematopoietic stem cell.

34. The method of claim 32, wherein the protein is globin.

35. A method of providing a functional protein to a subject in need of the functional protein comprising transducing the subjects' cells with the vector of claim 2, wherein the nucleic acid encodes a functional protein deficient in the subject, thereby providing the functional protein to the subject.

36. A method of providing an antisense nucleic acid to a subject in need of the antisense nucleic acid comprising transducing the subjects' cells with the vector of claim 2, wherein the nucleic acid encodes an antisense nucleic acid that diminishes expression of a protein in the subject, thereby providing the antisense nucleic acid to a subject in need of the antisense nucleic acid.

37. A method of treating, in a subject, a hemoglobin disorder characterized by a reduction or absence of a functional globin protein, comprising administering to the subject a hematopoietic cell to which the vector of claim 17 has been administered ex vivo, thereby expressing globin in the cell in the subject and providing functional globin protein to treat the subject.

38. The method of claim 37, wherein the gene is $^A\gamma$ globin.

39. The method of claim 37, wherein the nucleic acid encoding a globin is inserted 5' of the 3' regulatory element.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 20 base pairs

```
        ( B ) TYPE: nucleic acid
        ( C ) STRANDEDNESS: single
        ( D ) TOPOLOGY: linear ( x i ) SEQUENCE DESCRIPTION: SEQ ID NO:1:

GATGATATCG CCGCGCTCGT                                                          20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GGTCATCTTC TCGCGGTTGG                                                          20
```